United States Patent [19]

Bruck

[11] 4,122,348
[45] Oct. 24, 1978

[54] METHOD OF AND APPARATUS FOR CLASSIFYING BIOLOGICAL CELLS

[75] Inventor: Abraham Bruck, Haifa, Israel

[73] Assignee: Elscint, Ltd., Haifa, Israel

[21] Appl. No.: 782,320

[22] Filed: Mar. 29, 1977

[30] Foreign Application Priority Data

May 21, 1976 [IL] Israel .......................................... 49622

[51] Int. Cl.$^2$ ............................................. G01N 21/38
[52] U.S. Cl. ................................................. 250/461 B
[58] Field of Search ................ 250/302, 461 R, 461 B

[56] References Cited

U.S. PATENT DOCUMENTS

| 3,497,690 | 2/1970 | Wheeless, Jr. et al. | 250/461 B |
| 3,896,307 | 7/1975 | Trowe | 250/461 B |
| 3,971,952 | 7/1976 | Inbar et al. | 250/461 B |

*Primary Examiner*—Davis L. Willis
*Attorney, Agent, or Firm*—Donald M. Sandler

[57] ABSTRACT

Cells in a population labelled with a lipid soluble fluorescent dye and excited with a beam of polarized light can be classified according to the distribution of the state of polarization of fluorescence emitted by a cell. The intensities of fluorescence, polarized in directions parallel and perpendicular to the direction of polarization of the excitation beam, are measured simultaneously to obtain the state of polarization.

The state of polarization, so determined, bears a functional relationship to the fluidity of the plasma membrane of the cell and is thus a measure of the cell's function. Consequently, classification of cells in a population by the distribution of the state of polarization of the fluorescence emitted in response to their excitation enables different types of cells to be distinguished according to biological function. For example, white blood cells can be differentially analyzed using the method of the present invention.

30 Claims, 7 Drawing Figures

METHOD OF AND APPARATUS FOR CLASSIFYING BIOLOGICAL CELLS

CROSS-REFERENCES TO RELATED ARTICLES AND PATENTS (1) U.S. Pat. No. 3,971,952 entitled "Method of Detecting Abnormal Behavior of Mammalian Cells" issued to Inbar et al (2) Von Sengbusch, G. and Thaer, A., "Some Aspects of Instrumentation and Methods as Applied to Fluormetry at the Microscale", pp 31–39 (Germany)

(3) U.S. Pat. No. 3,699,336 entitled "Biological Cell Analyzing System" issued to Ehrilich et al (4) Shinitsky, M.; Dianoux, A. C.; Gitler, C.; Wever, G.: "Microviscosity and Order in the Hydrocarbon Region of Micelles and Membranes Determined with Fluorescent Probes. I. Synthetic Micelles", *Biochemistry*, Vol. 10, No. 11, pp 2106–2113 (1971)

BACKGROUND OF THE INVENTION

This invention relates to a method of and apparatus for determining the normality of biological cells.

In reference (1), which is hereby incorporated by reference, each cell of a population of biological cells, labelled with a lipid soluble fluorescent dye, is simultaneously excited by a beam of polarized light. Fluorescence emitted by the population is, itself, polarized; and the average state of polarization of this fluorescence is determined by the intensities of fluorescence, polarized parallel and perpendicular to the direction of polarization of the excitation beam. An analytical combination of the intensities determines the average state of fluorescent polarization in terms of fluidity, degree of fluorescent polarization, microviscosity, etc. as identified in reference (1).

It is known that the average state of polarization depends upon the cumulative nature of all of the plasma membranes of the cells in the population. The membrane of a cell is, fundamentally, a lipid bilayer in which protein molecules are embedded. This membrane play an important role in the metabolic activity of a cell in relation to its surroundings, since all interchanges between the cell and its surroundings must take place through the membrane. For this reason, the precise constitution of the membrane has been a most important object of cytological studies for a number of years. Reference (1) and a recent study reported in the *Journal of Molecular Biology*, volume 85, May, 1974, pp. 603–615, show that the state of polarization of fluorescence emitted by the cell population, (e.g., expressed in terms of the microviscosity of the entire population), is markedly different for normal and abnormal cell populations.

Useful conclusions can be drawn from the average state of polarization of fluorescence emitted by a population of cells. Were it possible to determine, accurately, the manner in which the state of polarization of fluorescence emitted by a cell is distributed throughout the cell population, as distinguished from the average state of polarization of the population as a whole, those cells in the population whose state of polarization differs from the population average could be quantified enabling conclusions to be drawn in evaluating the normality of the cell population. For example, the presence of malignant cells could be determined, or white blood cells could be differentially analyzed.

Microscope fluorometry is a technique for obtaining a measure of the state of polarization of fluorescence emitted by cells in a population; and is described in reference (2). In the conventional approach, cells labelled with a lipid soluble fluorescent dye are deposited on a slide operatively positioned relative to the objective of a microscope rigged to project a polarized beam of excitation radiation through the objective and onto a cell, or a portion of a cell, localized with respect to the objective. Associated with the objective is an imaging lens establishing a single output channel having a polarizer for polarizing the fluorescent output of the localized cell, and a rotatable analyzer for measuring the intensity of fluorescence polarized in directions parallel and perpendicular to the direction of polarization of the excitation beam. With this arrangement, the two output intensities are obtained sequentially. Consequently, the measurements will be sensitive to fluctuations in the intensity of the excitation beam, and the effect of time-dependence of the fluorescence itself due to bleaching of the dye, for example. In addition, inhomogeneities in the optical system with respect to polarization introduce further errors in the measured intensities. As a consequence, reliance cannot be placed on the measurements obtained, and definitive conclusions cannot be drawn.

It is therefore an object of the present invention to provide a new and improved method of and apparatus for determining the normality of cells wherein the deficiencies outlined above are overcome or substantially reduced.

SUMMARY OF THE INVENTION

The present invention provides a method for determining the normality of biological cells comprising the steps of labelling the cells with a lipid soluble fluorescent dye, depositing the cells in a region where they can be examined one at a time, exciting the cells with a beam of polarized light, and determining the state of polarization of fluorescence emitted by each cell from simultaneous measurements of the intensities of fluorescence polarized in directions parallel and perpendicular to the direction of polarization of the excitation beam.

The invention also consists in apparatus for determining the normality of biological cells. Such apparatus includes a fluorescent microscope having a polarized light source, and a microscope table which is operatively positioned relative to the objective of the microscope, and which can be selectively positioned in two dimensions relative to the objective. The output of the microscope is separated into two channels, each of which has a polarizer with its polarization axis oriented parallel and perpendicular, respectively, to the direction of polarization of the light source, and single-photon detectors are individually associated with each channel for measuring the intensity of light passing through the polarizer in the channel. By selectively positioning the table in two dimensions relative to the object, cells deposited on a slide and labelled with a lipid soluble fluorescent dye can be operatively positioned, or localized, sequentially, one-by-one, relative to the objective thereby. By making simultaneous intensity measurements in each channel for each cell, the state of polarization of fluorescence emitted by the cell can be determined.

Because the intensity measurements are made simultaneously, fluctuations in the intensity of the excitation beam and the effect of time-dependence on the fluorescent output do not affect accuracy. Furthermore, the use of two output channels allows each to be separately adjusted to compensate for inhomogeneities in the optical system in respect to the light polarization. As a consequence, the state of polarization of fluorescence emitted by the cells derived in the above manner, provides a direct correlation with the membrane fluidity enabling, for example, abnormal cells to be distinguished from normal cells on this basis.

BRIEF DESCRIPTION OF THE DRAWINGS

Embodiments of the invention are shown in the accompanying drawings wherein.

DESCRIPTION OF THE PREFERRED EMBODIMENTS

Figures 1, 2, 3:
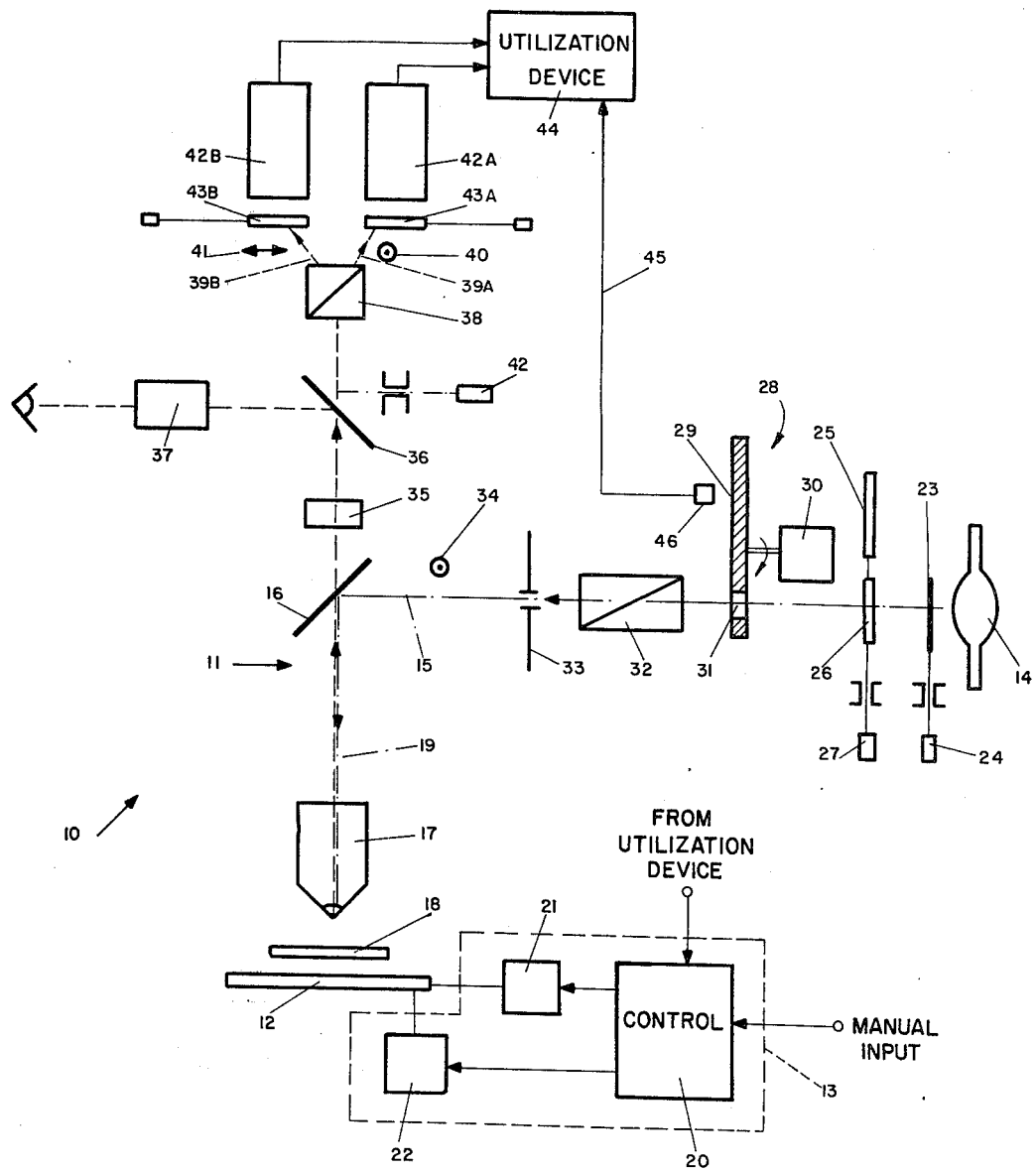
FIG. 1 is a simplified block diagram of apparatus in accordance with the present invention for classifying biological cells.
FIG. 2 is a composite of FIGS. 2A and 2B which, together, constitute a block diagram of the control for the measuring circuits of the apparatus shown in FIG. 1.
FIG. 3 is a composite of FIGS. 3A and 3B which, together, constitute a flow chart for illustrating the method according to the present ivnention for classifying cells.
Figure 2A:
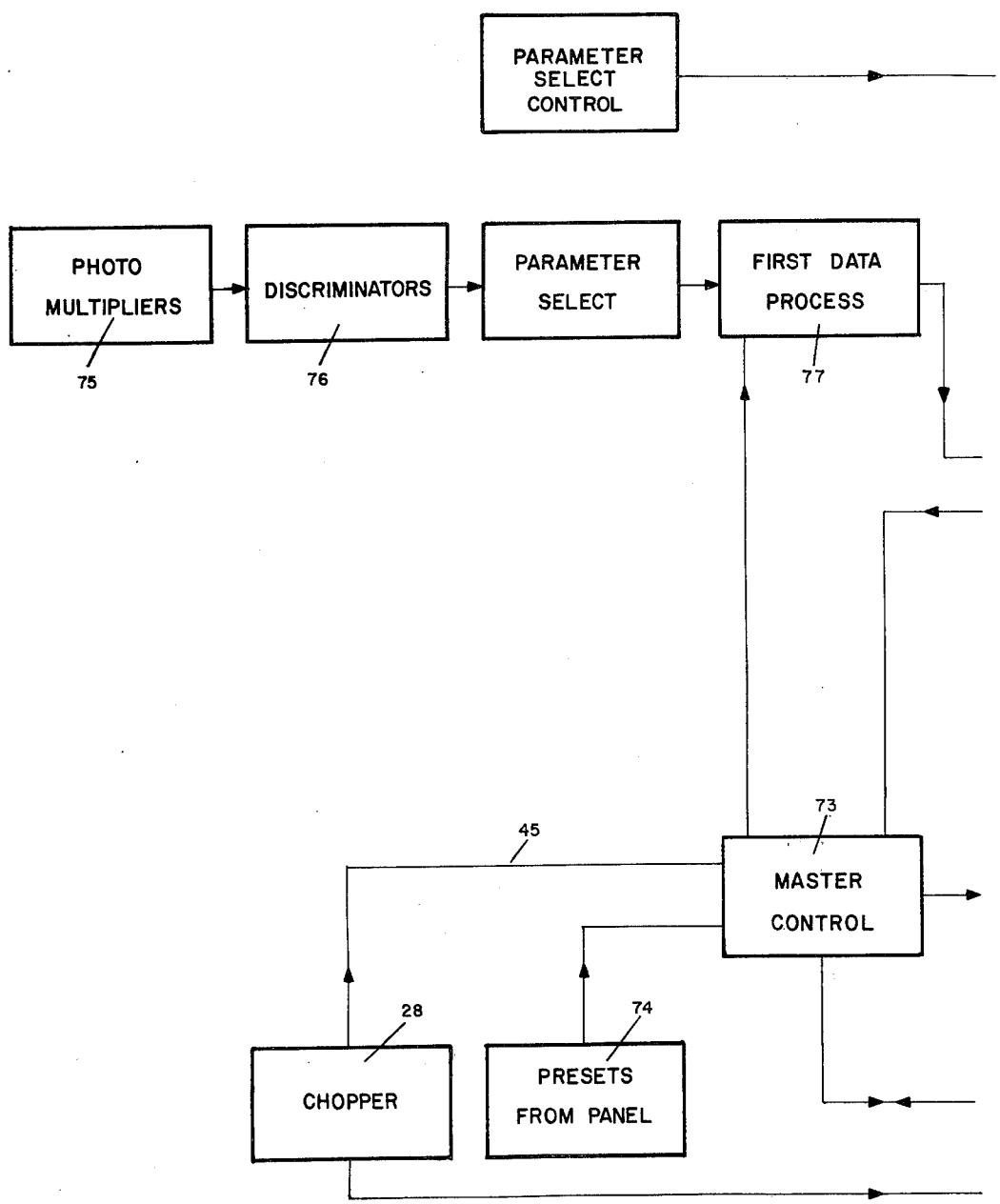
Figure 2B:
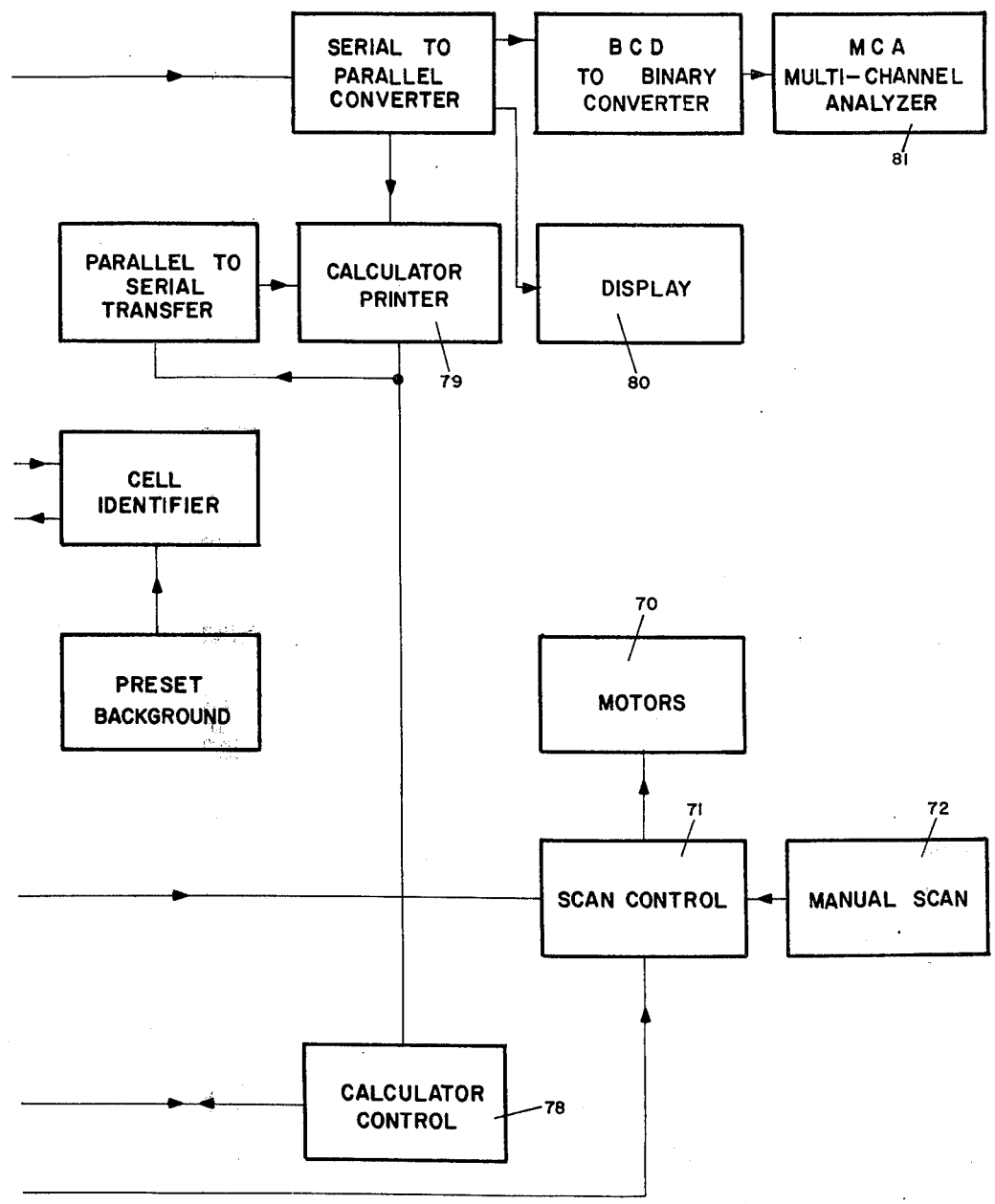
Figure 3A:
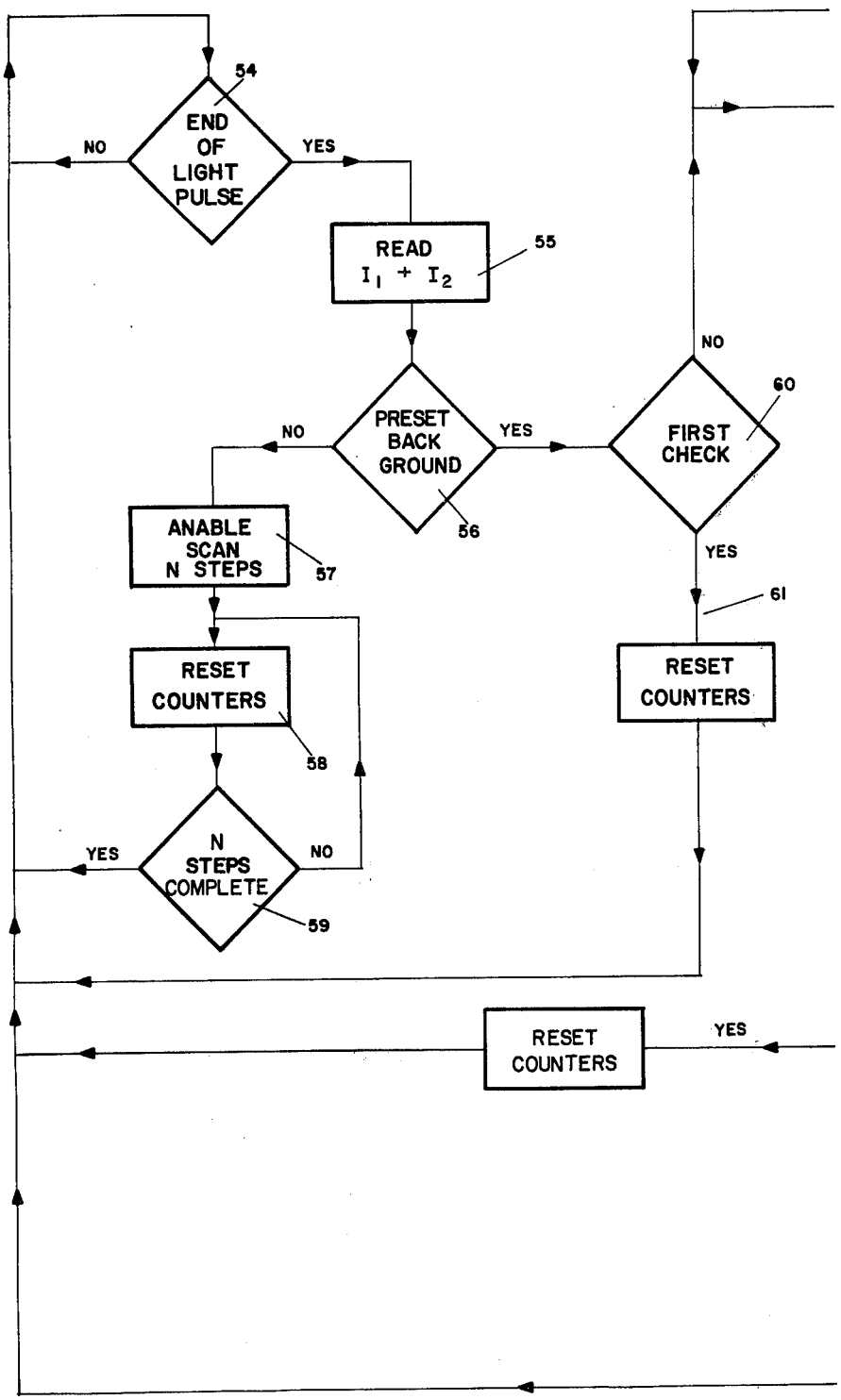
Figure 3B:
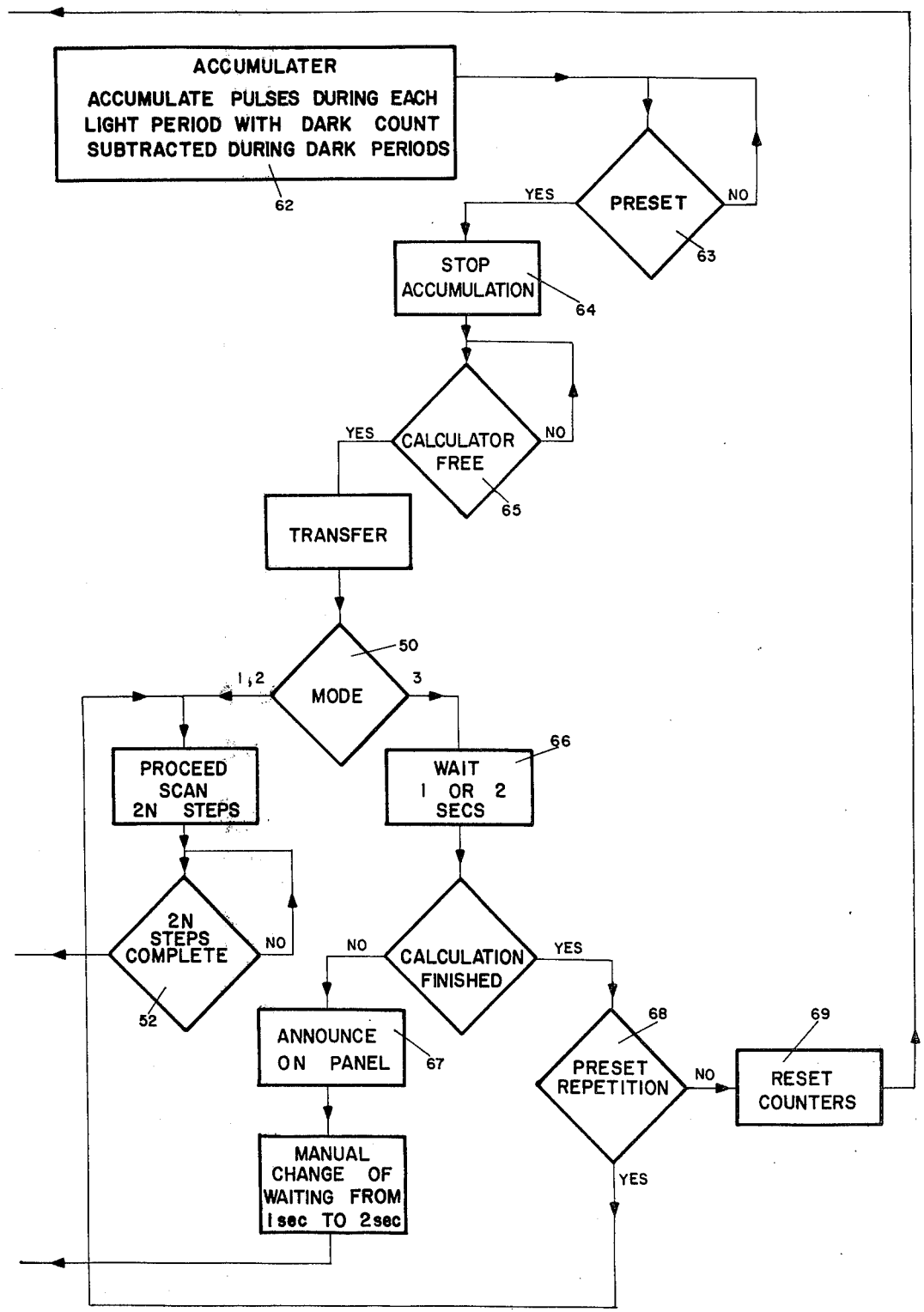

Referring now to FIG. 1, reference numeral 10 designates apparatus in accordance with the present invention for classifying biological cells. Apparatus 10 comprises fluorescent microscope 11, which may be similar to a microscope shown in U.S. Pat. No. 3,860,813, microscope table 12, and table positioning mechanism 13 which may be of the type disclosed in U.S. Pat. Nos. 3,851,972 and 3,892,484. Microscope 11 includes a light source 14 for directing light along horizontal axis 15 toward a dichroic mirror 16 where such light is reflected along vertical axis 19 into a non-fluorescent microscope objective 17 from which it exits and is incident on sample slide 18 carried by table 12. The sample slide, such as a hemacytometer slide, carries a population of treated cells deposited thereon as described below so that the can be examined one-at-a-time.

Microscope table 12 operatively supports slide 18 relative to the objective, and can be selectively displaced in a plane perpendicular to axis 19 in accordance with manual or automatic command signals applied to control 20 of mechanism 13. Control 20 selectively supplies pulses to X-stepping motor 21 and Y-stepping motor 22 in accordance with the command signals. Thus, table 12 can be selectively displaced in discrete steps in two dimensions to position any elemental area of the slide in operative relationship to the objective.

Light source 14 is preferably a high-pressure mercury lamp aligned with axis 15 for producing light having a component, for example, at 365nm wavelength. Shutter 23, selectively postionable relative to axis 15, can be moved out of blocking relationship with lamp 14 by means of operator 24. Downstream of shutter 23 is a filter station at which a dual filter is located, one of the filters 25 being for visible light, and the other filter 26 passing light of a wavelength that will excite the fluorescent dye used to label the cells under investigation. For the dye DPH(1.6-diphenyl 1,3,5,-hexatriene), the preferred excitation wavelength is 365nm.

Both filters are rigidly fixed together, and are movable as a unit by operator 27. The dual filter has a first position at which visible filter 25 is aligned with axis 15, and operative position at which filter 26 is aligned with the axis.

Downstream of the filter station is light chopper 28 comprising a disc 29 driven by motor 30 for periodically chopping the light passing the filter station. Disc 29 is provided with a plurality of apertures 31 so that light from lamp 14 intermittently passes along the optical axis 15 when motor 30 rotates disc 29. Beyond the chopper station is located a Glan-Thomson polarizer 32 for polarizing the light furnished to dichroic mirror 16. Finally, a field diaphragm 33 is interposed between polarizer 32 and the dichroic mirror for the purpose of controlling the illuminated area on the slide which thus can be limited to the size of a cell, or to a part of a cell. By reason of the operation of polarizer 32 when filter 26 is aligned with the optical axis, the light incident on dichroic mirror 16 will have a wavelength of 365nm and will be polarized. For reference purposes, the direction of polarization is shown at 34, this symbol indicating that the direction of polarization is perpendicular to the paper.

The light, polarized as indicated, is reflected by the dichroic mirror through objective 17 and onto the sample carried on sample slide 18. Assuming that a single cell labelled with a lipid soluble fluorescent dye has been localized relative to objective 17, i.e., has been positioned directly beneath the objective by reason of the operation of the slide table positioning mechanism 13, the polarized light incident on the labelled cell will excite the cell causing the latter to fluoresce. Fluorescent light, at a wavelength dependent on the fluorescent dye used to label the cells under investigation, will be emitted by the excited cell. For the dye DPH, the fluorescence will be about 420nm. Such fluorescence from the cell will enter objective 17 and pass upwardly along axis 19 through dichroic mirror 16 and through cut-off filter 35 which functions to eliminate specular reflections.

A set of prisms 36 is selectively movable into and out of alignment with axis 19 by manipulation of operator 42. When positioned on the axis, the prisms direct fluorescent light into eyepiece 37. When the prisms are removed from the axis, all of the fluorescent light passes into a Walaston prism 38 which divides the output of the microscope into two output channels 39A, 39B polarized at different angles. Specifically, and for the purposes of illustration only, the light passing through channel 39A is polarized in a direction perpendicular to the paper as indicated by symbol 40, while the light passing through channel 39B is polarized in a direction parallel to the paper as indicated by symbol 41. Note that light in channel 39A is polarized in a direction parallel to the polarization of the excitation light, and in channel 39B, the polarization is perpendicular to the polarization of the excitation light.

The state of polarization of the fluorescence emitted by an excited cell localized relative to objective 17 is determined by simultaneous measurements of the intensity of fluorescence polarized in directions parallel and perpendicular to the direction of the direction of polarization of the excitation beam 15. Such measurements are preferably carried out by utilizing single-photon counting techniques. Accordingly, each output channel contains a single-photon counting detector, such as a photomultiplier, designated 42A and 42B, respectively. Sheet polarizers 43A and 43B oriented to pass polarized light in the direction of polarization of channels 39A and 39B respectively, are located in front of detectors 42A and 42B respectively. The outputs of each of detectors 42A and 42B are connected to a utilization device 44, to which is also supplied a synchronizing line 45 connected to angular position detector 46 for the purpose of relating the instantaneous output of the two detectors.

Because two output channels 39A and 39B are utilized, measurements of the intensities of fluorescence polarized in directions parallel to and perpendicular to the direction of polarization of the excitation beam and be carried out simultaneously, eliminating from the data the influence of fluctuations in the intensity of the excitation beam during accumulation of data, and the influence of any time-dependence on the fluorescent output. The provision of adjustable polarizers 43A and 43B in the two channels enables the absolute values of light intensities reaching each detector to be controlled by rotating the polarizers thereby compensating for inhomogeneities in the optical system with respect to the light polarization. As a consequence, the data obtained using the apparatus of the present invention accurately reflect the membrane fluidity of each cell and enable abnormal cells to be distinguished from normal cells on a cell-by-cell basis.

It also should be appreciated that some modifications of means for controlling the number of counts per photons reaching each of the channels may be performed. As an example, they may comprise variable neutral density filters in front of each said detector or means for electronically controlling the duty cycle of data transfer from the detector to the utilization device.

By reason of the operation of chopper 28, the excitation light is periodically incident on a sample localized relative to objective 17. The chopping frequency is approximatly 200Hz; consequently, the fluorescent output passing into polarizer 38 has a period of about 5 msec with a 50% duty cycle. Each 2.5 msec burst of fluorescence is many times longer than the lifetime of the fluorescent dye used to label the cells under consideration. For DPH, the lifetime is of the order of 10 nsec.

In each of the three modes of operation of the instrument, described below, counts produced by a detector 42A or 42B during the time that an opening 31 is aligned with axis 15, (i.e., during a 2.5 msec interval that a cell is excited) are accumulated in a counter (not shown) associated with each detector and contained in utilization device 44. Synchronization information is obtained from the output of detector 46. During the time that disc 29 blocks the excitation light in channel 15 (i.e., during a 2.5 msec interval), counts produced by the detectors due to noise are subtracted from their associated counters. In this manner, low frequency internal noise can be eliminated.

The three moles of operation of the instrument are as follows:

Mode I — Preset total photon count.

In this mode of operation, the sum of the counts produced in each channel is preset. If the fluorescence intensities polarized in directions parallel and perpendicular to the direction of the excitation beam are designated $I_1$ and $I_2$, respectively, then for a Mode I operation, the accumulation of counts in the counters associated with detectors 42A and 42B is terminated when $I_1 + I_2$ equals the preset count.

Mode II — Preset time.

In this mode of operation, the output of the detectors 42A and 42B are gated into their associated counters for a preselected period of time. At the end of the gating period, the contents of the counters are representative of the fluorescence intensity polarized parallel ($I_1$) and perpendicular ($I_2$) to the polarization excitation, respectively.

Mode III — Preset periodic measurements.

In this mode of operation, either Mode I or Mode II methods of measurement are carried out successively at preset time intervals. That is to say, measurements are repeated, up to a preset number of times, at regular intervals of time in order to determine whether the state of polarization of fluorescence a cell is time dependent.

The second mode of operation is of importance because utilization of a Mode I method of measurement gives poor results for cells whose state of polarization depends on the excitation time. When such cells are examined using a Mode I operation, a strongly fluorescent cell will be illuminated for a short period of time while a weakly fluorescent cell will be illuminated for a longer period of time. Where the state of polarization is time-dependent, a Mode I measurement will produce inaccurate results. Therefore, a Mode III operation is usually carried out initially for the purpose of ascertaining whether a Mode I form of operation will provide accurate results.

In order to eliminate reflected and scattered light interference, a nanosecond light source can be utilized instead of steady-state light source 12 and chopper 25. In such case, no chopper is required, and the fluorescence would be measured after the excitation light pulse has terminated.

After one of the three above-described modes of operation of the instrument has been carried out in connection with a cell localized with respect to objective 17, the microscope table operating mechanism 13 is activated for the purpose of displacing table 18 relative to the objective until another cell is localized and the selected mode of operation repeated. This process of measuring $I_1$ and $I_2$ of a cell, and then moving the table until another cell is in position for measurement, is repeated until a representative number of cells in the population contained on slide 18 has been examined.

After $I_1$ and $I_2$ have been measured with respect to an individual cell, the state of polarization of the cell can be determined from which the fluidity, microviscosity, etc. can be calculated. For example, Reference (1) discloses how various cell parameters can be calculated from $I_1$ and $I_2$. The following relationship shows the connection between degree of polarization and microviscosity.

$$(1/P - 1/3) = (1/Po - 1/3)(1 + \frac{\tau}{\rho})$$
$$= (1/Po - 1/3)(1 + \frac{RT\tau}{\eta Vo})$$

where:
P = degree of fluorescent polarization
Po = limiting intrinsic polarization
$\tau$ = lifetime of excited state (for DPH, $\tau$ = 10 msec)
$\rho$ = rotational relaxation time
R = universal gas constant
T = absolute temperature
$\eta$ = microviscosity
Vo = volume of equivalent sphere After a representative number of cells have been examined, and the state of polarization of fluorescence the cells determined, the cells can be classified by the distribution of the state of polarization. It has been found that the classification of cells in the manner described above enables abnormal cells to be distinguished from normal cells, and thus provides guidance in determining the presence of malignant cells and enables white blood cells to be classified into different groups.

In order to examine the lipid layer of each cell in a population under consideration, a lipid soluble fluorescent dye, such as DPH, is added to a cell suspension in a phosphate buffered saline solution, and allowed to incubate for about an hour. Some of the suspension is then deposited on a slide in a region such that the cells can be examined one-at-a-time on the slide. When excited by polarized ultraviolet light, those fluorescent molecules whose absorption dipole happens to coincide with the direction of the electric vector of the excitation light will be preferentially excited. The Brownian motion of the fluorescent molecules causes a certain depolarization of fluorescent light emitted after de-excitation. This depolarization reflects the rigidity of the immediate surroundings of the fluorescent molecule, namely the cell membrane structure. In this manner, the nature of the membrane layer of the cell is determined.

The control circuit of FIG. 2 causes the apparatus shown in FIG. 1 to operate in accordance with the flow chart shown in FIG. 3 to which reference is now made. In response to the selection of a Mode I or Mode II operation at 50 in FIG. 3, an enabling signal is furnished to control 20 of microscope table operating mechanism 13 such that pulses are furnished to stepping motors 21 or 22 causing the table 17 to be displaced in one direction through 2N steps, where N steps represent the greatest linear dimension of a cell under consideration. The table movement is monitored as indicated by block 52, and when a determination is made that the 2N steps have been completed, a command signal is produced which resets the two counters associated with the detectors 42A and 42B, which counters are contained in utilization device 44 referred to above.

After the counters have been reset, the apparatus enters a testing sub-routine to determine if a cell has been localized beneath the microscope objective. A determination is made at 54 on whether a light pulse arising from the action of chopper 28 has terminated. Data from detector 46 is utilized for this purpose. If the pulse is not terminated, the counters continue to accumulate counts; and upon the end of the light pulse, the contents of the two counters are added together as indicated as 55. The symbols $I_1$ and $I_2$ represent the fluorescent signals from detectors 42A and 42B respectively and constitute orthogonal components of the intensities of the fluorescent output of the microscope; and if the sum of the contents of the counters is less than a preset number, which is representative of the absence of a cell beneath objective 17, then the conclusion is that the microscope table mechanism has not positioned a cell beneath the objective. Accordingly, an enabling signal is furnished to control 20 which responds by causing the microscope table stepping motors to index 2N steps in the search for the next cell to be examined. This is indicated at 57, and following this, the counters are reset as indicated at 58 in preparation for testing for the presence of a cell. The sensing means associated with the table determines whether the indexing is complete as indicated at 59. When the step is complete, the testing sub-routine is again carried out utilizing 54, 55, 56 and 57. This sub-routine is carried out until the table is positioned such that the sum of the counters exceeds a preset value, i.e., until a cell is located beneath the objective. If made necessary by the distribution of cells on the slide, the table may be moved to its maximum displacement in one direction; and in such case, this is sensed and the table is indexed through N steps in an orthogonal direction as a rectangular raster is traced during the search for the next cell.

When the testing sub-routine determines that a cell is positioned beneath the objective, a control flip-flop may be set in order to permit verification that a cell is, in fact, present beneath the objective. Thus, the contents of the counters are not utilized for data accumulation the first time a cell is detected; and the procedure is by way of path 61 which allows the counters to be reset so that, at the termination of the next light pulse, the contents of the counters can be added together to verify the previous results. If the results are positive, the apparatus enters a data accumulation sub-routine at 62.

In the data accumulation sub-routine, counts are accumulated during the periods that the chopper delivers excitation light to the cell, and subtracted during the periods that the chopper blocks the excitation light. Since the instrument is operating in either Mode I or Mode II, either a preset time or a present count is in effect at 63. When this preset number has been reached, further accomulation is halted at 64, and the contents of the counters are saved by transferring the contents into buffers. When the calculator associated with the instrument is free, as indicated at 65, then the contents of the buffers are transferred to storage for later processing.

If Mode III operation had been selected at 50, then a small delay occurs as indicated by 66 to determine whether any calculation that is in process is finished. If it is not, then a panel light may be illuminated as indicated by 67 to advise the operator of this condition giving him the option of changing the waiting period referred to at 66. The sub-routine in connection with positioning the next cell beneath the objective then takes place in the manner described above using 54–57. When a cell is positioned beneath objective 15, the data accumulation sub-routine is entered; and when the first preset count or preset time is reached, 63 is effective to make the determination and the contents of the counters are transferred first to buffers and then to storage. At that point, 68 determines whether the Mode III operation is finished; and if it is not, then the counters are reset as indicated by block 69 and the data accumulation sub-routine is repeated until the preset condition at 68 has been detected. The apparatus then reverts to its testing sub-routine, etc.

Referring now to FIG. 2 of the drawing, which shows the control system for carrying out the operations shown in FIG. 3, block 70 schematically represents the microscope table stepping motors, which in FIG. 1 have been designated 21 and 22. The motors are operated by scan control 71 either by a manual operation as indicted by 72 or under the autiomtic control of master controller 73. The present inputs to the system are indicated at 74, such presets relating to the preset background shown in FIG. 3 at 56 as well as the preset condition shown at 63 and 68. The chopper 28 shown in FIG. 1 is also shown in FIG. 3, and the synchronizing signals are applied to master control 73 as well as to the scan control 71.

Data acquisition is obtained from the photomultipliers 75 to which discriminators 76 are connected. The block marked 77 contains the counters and buffers as well as the suitable memory storage locations necessary to store representatives of $I_1$ and $I_2$ for each cell. The actual calculations of fluidity, degree of fluorescent polarization, etc. are carried out by calculator 78. The data to be displayed is operated on for display purposes and is available from printer 79 of CBT display 80. Alternatively, a multi-channel analyzer 81 can be employed for the purpose of plotting the distribution of the characteristic properties of the cell population.

As an alternative to the smearing of the labelled cells on a slide, which is displaced in two dimensions relative to the objection of a fluorescent microscope, the one-by-one examination of the cells of a population can be carried out by flowing the cells in single file through a constriction housing a quartz window which is transparent to ultraviolet radiation. The cells would pass slowly through the constriction allowing excitation and fluorescence to take place in the constriction.

By the use of a fluorescent microscope and an indexable table, specific cellular regions can be examined rather than a complete cell. For this reason, the term "cell-by-cell", to describe the measurements means measurements made on an entire cell or on a specific intercellular region of the cells.

It is believed that the advantages and improved results furnished by the method and apparatus of the present invention are apparent from the foregoing description of the several embodiments of the invention. Various changes and modifications may be made without departing from the spirit and scope of the invention as sought to be defined in the claims that follow.

What is claimed is:

1. In a method for classifying biological cells which have been labelled with a lipid soluble fluorescent dye and deposited in a region so that they can be examined one-at-a-time, and which are excited with a beam of polarized light, the improvement comprising determining the state of polarization of the fluorescence emitted by each individual cell in a population by simultaneously measuring the intensities of fluorescence polarized in directions parallel and perpendicular to the direction of polarization of the excitation beam.

2. A method according to claim 1 wherein said property is measured by separating the light emitted by an excited cell into two channels that pass light polarized in directions parallel and perpendicular to the direction of polarization of the excitation beam, and simultaneously measuring the intensity of the polarized light in each channel.

3. A method according to claim 2 wherein the intensity in each channel is obtained by a single-photon counting technique.

4. A method according to claim 3 wherein photons counted in each channel during the excitation time are accumulated, and photons counted in each channel during the non-excitation time are subtracted from the respective counts accumulated during the excitation times.

5. A method according to claim 4 wherein the counts are accumulated in each channel until the sum of the counts reaches a predetermined number.

6. A method according to claim 4 wherein the counts are accumulated in each channel for a predetermined interval of time.

7. A method according to claim 4 wherein the photons are counted over equal intervals of time relatively long with respect to the period of the light incident on a cell, such equal intervals of time being separated by time intervals during which no photons are counted.

8. A method according to claim 1 wherein the deposition of the cells is done by smearing them on a microscope slide.

9. A method according to claim 1 wherein the deposition of the cells is done by flowing them through a constriction wherein the excitation takes place.

10. A method according to claim 1 wherein the cells are deposited on a hemacytometer slide in order to keep them intact.

11. In a method for classifying a population of biological cells which have been labelled with a lipid soluble fluorescent dye and deposited in a region so that they can be examined one-at-a-time, and which are excited with a beam of polarized light, the improvement comprising: determining the state of polarization of the fluorescence emitted by each individual cell in a population by simultaneously measuring the intensities of fluorescence polarized in directions parallel and perpendicular to the direction of polarization of the excitation beam of the individual cells.

12. A method for classifying biological cells into different groups comprising the steps of:
   a. labelling the cells with a lipid soluble fluorescent dye;
   b. depositing these cells in a region so that they can be examined one-at-a-time;
   c. exciting at least a portion of each of the cells with a beam of polarized light; and
   d. simultaneously measuring, for the fluorescence emitted by each cell, the intensities of fluorescence polarized in directions parallel and perpendicular to the direction of polarization of the excitation beam for determining the individual state of polarization of each cell in the region.

13. A method according to claim 12 wherein the excitation of the cells is done on a cell-by-cell or a fraction of a cell basis.

14. A method according to claim 13 wherein the excitation light incident on a cell is periodic.

15. A method according to claim 14 wherein the excitation light is chopped.

16. A method according to claim 14 wherein the excitation light is pulsed.

17. A method according to claim 12 wherein the biological cells are from a human female genital tract.

18. A method according to claim 12 wherein the biological cells are leucocytes (white blood cells).

19. Apparatus for determining the type of biological cells comprising:
   (a) a fluorescent microscope having a light source for directing a beam of polarized light into an objective through a dichroic mirror which passes light picked up by the objective into an output path;
   (b) a microscope table operatively positioned relative to the objective and adapted to hold a slide on which are deposited cells labelled with a lipid soluble fluorescent dye;
   (c) means for selectively positioning the table in two directions relative to the objective;
   (d) means in the output path of the microscope for separating the light therein into two channels respectively polarized parallel and perpendicular to the direction of polarization of said beam; and
   (e) a single photon counting detector associated with each channel for simultaneously measuring the light intensity in the two channels.

20. Apparatus according to claim 19 wherein selectively adjustable means are associated with the two channels for controlling the number of counts per photon incident on the detectors.

21. Apparatus according to claim 19 wherein the means for selectively positioning the table automatically positions the table to sequentially localize the cells on said slide in operative association with the objective.

22. Apparatus according to claim 21 including means responsive to completion of the measurement of light intensity in the two channels when the table is positioned to localize a cell for moving the table through a predetermined displacement.

23. Apparatus according to claim 22 wherein the means for selectively positioning the table includes means for displacing the table until $I_1 + I_2$ exceeds a threshold and holds the table fixed for said predetermined time interval whereby the cell in the population on the slide can be sequentially localized in operative association with the objective.

24. Apparatus according to claim 23 wherein the means responsive to the light intensities in the two channels includes means for adding two intensities and means for determining when the sum exceeds a threshold.

25. Apparatus according to claim 19 including means for causing the polarized light directed into the objective to be periodic.

26. Apparatus according to claim 25 including a light chopper interposed between the source and the objective for periodically furnishing excitation light to the objective.

27. Apparatus according to claim 26 including means associated with each detector for accumulating the number of photons received during the intervals that the excitation light is furnished to the objective, and for subtracting counts from the accumulation during intervals that excitation light is not furnished to the objective.

28. Apparatus according to claim 27 including means for accumulating counts from each detector up to a predetermined number.

29. Apparatus according to claim 25 wherein the light source is pulsed.

30. In a method for classifying a population of biological cells which have been labeled with a lipid soluble fluorescent dye and deposited in a region so that they can be examined one-at-a-time, and which are excited with a beam of polarized light, and wherein the intensities of fluorescence polarized in directions parallel and perpendicular to the direction of polarization of the excitation beam are measured for determining the state of polarization of fluorescence emitted by each cell in the population, the improvement being: classifying each cell in the population into different groups according to the state of polarization of fluorescence emitted by the cell.

* * * * *